United States Patent [19]

Mitchell et al.

[11] Patent Number: 5,352,467
[45] Date of Patent: Oct. 4, 1994

[54] IN SITU METHOD FOR PROCESSING A PERISHABLE PRODUCT

[75] Inventors: Jerry L. Mitchell, Livingston, Tex.; A. James Farr, Baton Rouge, La.; Kenneth W. McMillin, Baton Rouge, La.; John H. Wells, Baton Rouge, La.

[73] Assignee: Pakor, Inc., Livingston, Tex.

[21] Appl. No.: 880,869

[22] Filed: May 11, 1992

Related U.S. Application Data

[60] Continuation-in-part of Ser. No. 510,947, Apr. 19, 1990, abandoned, which is a continuation of Ser. No. 214,195, Jun. 27, 1988, Pat. No. 4,919,955, which is a division of Ser. No. 94,384, Sep. 8, 1987, abandoned.

[51] Int. Cl.$^5$ .............................................. B65B 31/04
[52] U.S. Cl. ...................................... 426/316; 53/434; 53/512; 426/320; 426/326; 426/392
[58] Field of Search ............... 426/316, 320, 326, 335, 426/392, 418; 53/432, 434, 512

[56] References Cited

U.S. PATENT DOCUMENTS

| | | | |
|---|---|---|---|
| 2,546,568 | 3/1951 | Taylor | 426/316 |
| 3,597,235 | 8/1971 | Kramer | 426/326 X |
| 4,744,199 | 5/1988 | Gannon | 53/434 |
| 4,919,955 | 4/1990 | Mitchell | 426/316 X |

*Primary Examiner*—Leo B. Tentoni
*Attorney, Agent, or Firm*—Gregory M. Luck

[57] ABSTRACT

A method is disclosed for enhancing the marketable characteristics for a given perishable product prior to or after the product has been placed in a gas-tight consumer-ready package. More specifically, the method of the present invention contemplates the use of one or more agents or mixtures thereof which are introduced into gas communication with a perishable meat product in a selected concentration based on a number of variables including moisture content, muscle type and surface area of said product.

19 Claims, No Drawings

IN SITU METHOD FOR PROCESSING A PERISHABLE PRODUCT

CROSS REFERENCES TO RELATED APPLICATIONS

This application is a continuation-in-part of applicant's co-pending application Ser. No. 510,947, filed Apr. 19, 1990, now abandoned which is a continuation of application Ser. No. 214,195, filed Jun. 27, 1988, now U.S. Pat. No. 4,919,955, which is a divisional of application Ser. No. 94,384,filed Sep. 8, 1987, now abandoned. The disclosure of the aforementioned applications is herein incorporated by reference.

BACKGROUND OF THE INVENTION

1. Field of the Invention

The present invention generally relates to a method for enhancing the marketable characteristics of a given product, and especially a perishable product, by exposing said product to one or more selected agents (e.g., a liquid, vapor, aerosol, or gas) in a predetermined, sequential order of delivery and exposure, while said product is maintained within a sealed, consumer-ready package. More specifically, the present invention relates to in situ method for processing a perishable product, where said method contemplates the employment of one or more chemical agents specifically selected for use with a given product, where said agent(s) are applied to the product while it is maintained within a sealed gas tight container, where further said agent(s) are employed at a selected concentration, temperature, pressure, and for a time sufficient to establish a predetermined modification of the particular product for retail presentation.

2. Description of the Prior Art

Perishable products, specifically meat, poultry, or fish products, are generally cleaned and packaged in bulk at a slaughter house or other processing facility preparatory to shipment to various retail outlets. These products are commonly packaged in containers such as plastic wrapped trays, pouches of plastic, paper or plastic coated paper bags, food storage tubes and the like. Upon reaching the retail outlet, the products are sorted, cut or otherwise handled for repackaging into containers that are typically pliant relative to rigid cans, bottles and cans in that they are flexible or soft to the touch. These containers are frequently transparent, as in the case of meats and poultry, to enable retail customers to view the product. Such products, especially meats, are commonly packaged in the ambient air atmosphere naturally occurring at such facilities.

Packaging of perishable products in such a fashion, however, ordinarily results in a fairly rapid reduction of the quality of the product as the product begins to age on the shelf with a resultant unacceptable appearance, smell and taste associated with bacterial chemical or biochemical deterioration. This phenomena occurs, though at a slower pace, even when such products are maintained in a refrigerated condition.

Product spoilage is partially a result of the multiplication of bacteria introduced onto the surface of the product during processing. Contamination of this sort is particularly pronounced in the processing of poultry. Moreover, the atmosphere introduced into the container of all perishable products also contributes to bacterial deterioration since such atmosphere contains a variety of airborne bacteria. Spoilage is also enhanced by "cross contamination" which is often brought about as a result of the common handling of products by human or mechanized devices during the packaging stage.

The rate and extent of lipid oxidation, color degradation, bacterial growth, texture changes and dehydration determines in large part the shelf life of the product. In this connection, a perishable product is generally considered to have a shelf life determined by the amount of time necessary for the deterioration to reach proportions which render the product unfit for consumption. This shelf life varies depending on the product and the conditions under which the product is processed and packaged. Fish and poultry traditionally have very short shelf lives when stored in an unfrozen state, whereas the shelf life for meat is generally somewhat longer. Regardless of the type of product, however, the presence of certain bacteria, especially pathogenic bacteria, can render the product dangerous for consumption even when present in small amounts. As a result of the above described problems relating to bacterial growth and other deteriorative changes, perishable products are generally refrigerated or frozen to enhance their shelf life.

A lowering in temperature is effective to retard the deterioration in the quality of the produce since lipid oxidation, color degradation, bacterial growth, and texture deterioration are slowed. For this reason, a perishable product generally will not spoil if frozen, but will almost immediately spoil if stored at room temperature in the absence of preservatives. However, even under frozen conditions, other quality properties other than microbiological deterioration may be sacrificed and thus render the product less usable after storage.

A number of techniques have evolved to utilize the benefits of freezing. One commercial preservation and storage method involves subjecting various products, especially fish and poultry, to temperatures slightly below 32° F. (0° C.). This technique, often referred to as "crusting" literally involves the freezing of the outer layer of the product. Products subjected to this technique are "slacked out" and displayed for sale in a refrigerated, non frozen state. Bulk retail and institutional packages of various perishable products are sometimes handled in this fashion.

Some products, however, especially poultry products, are felt to deteriorate in quality once subjected to freezing. Additionally, it is often times undesirable to freeze a product if further processing is contemplated at a secondary processing facility. For these reasons, other techniques have been developed to store or transport the product while maintaining the product at temperatures above freezing.

One such technique is vacuum packing. Vacuum packing inhibits bacterial growth by removing the operative oxygen environment necessary to sustain aerobic growth. Disadvantages with vacuum packing, however, include the purplish color induced in meat products which often times diminishes the appearance of such products for purposes of retail sale. Vacuum packing also results in the creation of an undesirable liquid exudate which is caused by package pressure differential. If commercial sale of vacuum packed products is desired, the product also must often be removed from the vacuum pack and exposed to oxygen so that the meat may "bloom." When exposed to oxygen, however, surface bacteria derived from the processing or packing operation, but keep in check during vacuum packaging, are then able to multiply and soon begin to move the product toward spoilage.

Other non-frozen techniques involves packing the product in a carbon dioxide atmosphere. A $CO_2$ atmosphere, like the vacuum pack, also inhibits the growth of aerobic bacteria. Thus the product, when exposed to an aerobic environment, begins to rapidly degrade as a result of residual bacteria. Additionally, the product often absorbs the $CO_2$, thus creating a negative pressure differential within the package and thereby making the package prone to collapse.

The above described techniques are useful, therefore, only from the standpoint of marginally prolonging the life of a perishable product during shipping, or when it is otherwise possible to maintain an aerobic environment around the product. Moreover, these techniques fail to inhibit the growth of anaerobic bacteria and do not maintain other desired quality characteristics important in retail sale.

Ozone ($O_3$) has long been widely used as an oxidizing agent for bacterial, virus, and mold control for meat and fish storage, fresh fish processing, produce storage, restaurants, cooling towers, animal feed products, marine life, beverage containers, swimming pools, potable water systems, and tertiary waste systems. Ozone is also currently widely used for odor control in air conditioning systems, industrial processing operations, restaurants, mortuaries, rest homes and other applications. Ozone gas is a very strong oxidizing agent, having an oxidation potential more than twice that of chlorine and approximately three times that of hydrogen peroxide. Ozone also has the advantage of breaking down upon use as an oxidant into oxygen, which is normally beneficial. The use of ozone for the sterilization or preservation of food products is generally described in U.S. Pat. No. 4,549,477, which discloses both the historical applications (batch process) as well as the application of ozone in a continuous process whereby the perishable product is moved through a treatment zone filled with ozone.

Disadvantages associated with the techniques described in the '477 patent includes the possibility of recontamination of the product after it is moved out of the ozone flushed region and into a packaging area. This possibility of contamination is enhanced if the product is not already positioned in the package but must be positioned either mechanically or manually. Further, the aforedescribed processes do not allow for the possible retention of the activity of the agent to be maintained by confinement to the smaller space involved with a product in a retail package.

SUMMARY OF THE INVENTION

The present method addresses the above noted and other disadvantages by providing a method to substantially modify a given product once it is sealed within a consumer-ready package. With specific regard to perishable products, the present invention presents the advantage of enabling the non-frozen shelf life of a perishable product to be significantly enhanced. In this connection, the present method enables the storage of products at temperatures above those ordinarily believed necessary to prevent spoilage.

The method of the present invention also contemplates the processing of a varied range of products, specifically perishable products, so as to enhance their color, smell, texture, appearance and other such characteristics while the products are maintained within a sealed container.

In a general aspect of the invention, a method is provided whereby a product, specifically including a perishable product, is selectively exposed to one or more agents for a time calculated to produce a predetermined change in the appearance and physical character of the product. This exposure is preferably conducted in an ordered, sequential fashion beginning with exposure of the product to a first agent at the time it is first sealed within the package, which first agent is preferably maintained within said package and ultimately modified or removed during the time the product is transported and ultimately presented to the consumer.

More specifically, the present invention is directed to a in situ method of processing a product, specifically including a perishable product, within in a gas-tight, consumer-ready package, which method comprises first subjecting the product to an atmosphere containing one or more chemical agent(s), where such agents are selected to have a maximum beneficial end result on each given product, and where such agents are applied in a selected order, and at selected concentrations, pressures and temperatures. These variables for the application of specific agents for the most part depend on the physical nature of the product itself, e.g. the type of product, the moisture content and fat content. The method of the present invention extends the products' shelf life by substantially reducing the microbial activity on the surface of the product. Alternatively or additionally, the method of the invention may enhance such aesthetic characteristics of the product such as color, smell or taste as indicated above.

The method of the present invention has a number of advantages over the art. With respect to perishable products, one such advantage is the ability to significantly reduce or eliminate the number of aerobic an anaerobic microorganisms present on the surface of such a product after the product has been sealed within a container. In such a fashion, the shelf life of the product can be substantially increased. Further, since the product remains in the sealed package, there is little possibility of recontamination. Moreover, since the product is treated in situ in the consumer-ready package, lower concentrations of the chemical agent are required to produce a desired treatment. In such a fashion, waste of the costly enhancement agents can be minimized. Moreover, when the present method is used in combination with conventional preservation techniques such as freezing, an even greater shelf life may be realized.

Further, the elimination or substantial reduction in the number of surface bacteria resultant from the present method allows for the storage of some perishable products for extended periods of time without the need for refrigeration. This is beneficial in remote areas of the world or in the event that refrigeration facilities are unavailable or temporarily disabled.

The present invention also provides for means to alter other aesthetic characteristics, e.g. color, texture, smell, of a given product so as to enhance its appeal upon presentation to the consumer.

Other objects and advantages of the invention will become apparent from the following detailed description of the preferred embodiment.

DETAILED DESCRIPTION OF THE PREFERRED EMBODIMENT

In one preferred embodiment of the present invention, a given product, e.g., a fatty beef product, is prepared for shipment to a retail facility, e.g. a grocery facility, for ultimate presentation to the consumer. For obvious reasons, it is desired to maintain the maximum freshness of the meat product during the time it is transported from the slaughterhouse to the retail outlet. In such a fashion the product is afforded a maximum shelf life.

The first step of such a method is to seal the product in a fluid tight container while the product is exposed to an oxidizer, e.g. $O_3$, $F_2$, $H_2O_2$, $KMnO_4$, $HOBr$, $HOCl$, $Cl_2$, $ClO_2$, $O_2$, $Br_2$ or $I_2$. By exposure to one or a combination of such oxidizers, the microbial presence on the exterior of the product will be substantially reduced or even neutralized. Moreover, by sealing both the oxidizer and the product within the container, the residence time of the oxidizer may be strictly controlled.

To enhance the effectiveness of the oxidizer, it may be desirable, once the package is sealed, to introduce a higher concentration of the same or a different agent into the sealed package. To further enhance the effectiveness of such an oxidizer, it may also be desirable to increase the pressure within the package beyond a single atmosphere. Still alternatively, it may be desirable to increase the temperature of the meat product and thereby expedite the oxidation process within the sealed package. In still a further embodiment, it may also be desirable to employ infrared or ultraviolet radiation to said product to inhibit microbial activity on a given product.

To ensure that the product is uniformly exposed to a given agent, e.g. an oxidizer, the package preferably includes a bottom tray which is provided with a series of raised knobs or ridges. To further ensure that the product receives maximum exposure to the agent, the package, once sealed, may also be vibrated or oscillated for a short period of time during the packaging or transport stage, so as to vary the contact zones between the raised knobs or ridges and the product.

While exposure of the product to an oxidizer is beneficial from the standpoint of eliminating most surface microbial activity, it is usually desirable to remove or reduce the oxidizer after a selected residence time. The length of this residence time will depend on such factors as the nature of the product, the mass of the product, the fat content of the product, the water content of the product, the temperature at which the product has been maintained, and the identity and concentration of the oxidizer. Once this residence time has been achieved, it is desirable to remove the oxidizer from the package without disrupting the sealed integrity of the package itself. This is preferably achieved by extracting the oxidizer through a septum valve or other similar resealable valve disposed in the walls of the package.

Once the oxidizing agent is withdrawn, it may be desirable to introduce a second agent into the package to further minimize microbial activity on the product, or to inhibit the growth of bacteria during product presentation. These agents may include a $CO_2$ mixture or a second, weaker oxidizer.

Preparatory to presenting a beef product to the consumer, it is often desirable to enhance the aesthetic characteristics of the product for maximum consumer appeal. This may be accomplished by exposing the product to a different agent which possesses a high $O_2$ content. Oxygen causes the meat product to "bloom", or assume a bright red color. This bright red color is generally indicative of the freshness of the meat product and is therefore desirable to the consumer.

Multiple variations of the above described technique may be employed with any number of different perishable products. For example, if it is desired to process a perishable fish or poultry product, it may be necessary to alter the above method to change the concentration of the agent and/or the residence time. Further, in the case of fish or poultry products, which tend to degrade at a much faster rate than do meat products, there is necessarily an increased emphasis on inhibiting bacterial growth during transportation and storage of the product preparatory to retail sale. Hence, it may be desirable to maintain a weak oxidizer within the package during the transportation and storage phases. With poultry and fish products, however, it is unnecessary to induce a "bloom" in the product.

Aside from the above described deteriorative effects associated with bacterial spoilage, perishable products, including beef products may often adopt a color, odor or texture which does not accurately reflect their freshness and fitness for consumption. Consequently, the sale of such products is often inhibited as a result of such aesthetic characteristics. It may therefore be desirable to treat these products with yet another, independent agent which, while it has no appreciable effect on the spoilage of the product, serves to enhance the characteristics usually deemed important for retail presentation and consumption of such products. Such agents may include ascorbic acid, isoascorbic acid, erythorbic acid, lactic acid, citric acid, succinic acid or mixtures of salts thereof. Alternatively, other agents such as glycerol monolaurate, sodium sorbate, sodium acetate, sodium iodacetate, potassium sorbate, potassium acetate, potassium iodecetate, iodoacetomide or mixtures or acidic solutions thereof may also be used.

We claim:

1. A method for processing a perishable meat product comprising the steps of:
    sealing the meat product in a consumer-ready package, where said package is provided with a resealable valve;
    introducing a first agent into said package through said resealable valve where said agent is selected to reduce the microbial activity present on the surface of said meat product, where further said agent is introduced at a selected concentration as determined by the weight and type of said meat product;
    maintaining said first agent in said package for a residence time determined on the basis of the type and concentration of the agent;
    extracting said first agent from said package through said valve and replacing it with a second agent where said second agent is adapted to inhibit microbial activity on the surface of said meat product, where further the concentration of the second agent is determined on the basis of the weight of said product;
    replacing said second agent with a third agent, where said third agent includes a high $O_2$ content and is adapted to induce a bloom in the meat product.

2. The method of claim 1 where said first agent is drawn from the group consisting of $O_3$, $F_2$, $H_2O_2$, $KMnO_4$, $HClO$, $Cl_2$, $ClO_2$, $O_2$, $Br_2$ and $I_2$.

3. The method of claim 1 further including the step of introducing yet a fourth agent into said sealed package to enhance the aesthetic characteristics of said meat product, where said agent is drawn from the group consisting of ascorbic acid, isoascorbic acid, erythorbic acid, lactic acid, citric acid, succinic acid and mixtures of salts thereof.

4. The method of claim 1 further including the step of introducing yet a fourth agent into said sealed package to enhance the aesthetic characteristics of said meat product, where said agent is drawn from the group consisting of glycerol monolaurate, sodium sorbate, sodium acetate, sodium iodacetate, potassium sorbate, potassium acetate, potassium iodacetate, iodoacetomide and mixtures of acidic solutions thereof.

5. A method for processing a perishable product comprising the steps of:
positioning the product in a gas impermeable package in gas communication with a selected first agent and thereafter sealing said package while gas communication is maintained between said product and said agent, where the concentration of said first agent is determined by the physical nature of the product.

6. The method of claim 5 where said agent is drawn from the group consisting of $O_3$, $F_2$, $H_2O_2$, $KMnO_4$, $HClO$, $Cl_2$, $ClO_2$, $O_2$, $Br_2$ and $I_2$.

7. The method of claim 6 in which said agent is either liquid or aerosol.

8. The method of claim 5 including the additional step of removing said first agent from said sealed package through a valve disposed in said package.

9. The method of claim 8 further including the step of replacing said first agent with a second agent so as to enhance the aesthetic characteristics of the product, where said second agent is drawn from the group consisting of ascorbic acid, isoascorbic acid, erythorbic acid, lactic acid, citric acid, succinic acid and mixtures of salts thereof.

10. The method of claim 8 further including the steps of introducing yet a third agent into said sealed package to enhance the aesthetic characteristics of said product, where said agent is drawn from the group consisting of glycerol monolaurate, sodium sorbate, sodium acetate, sodium iodacetate, potassium sorbate, potassium acetate, potassium iodacetate, iodoacetomide, and mixtures of acidic solutions thereof.

11. A method for processing a perishable product comprising the steps of:
sealing the product in a consumer-ready package;
introducing a first agent into said package where said agent is selected to reduce the microbial activity present on the surface of said product, where further said agent is introduced at a selected concentration as determined by the physical nature of said product;
maintaining said first agent in said package for a residence time determined on the basis of the type and concentration of the agent;
extracting said first agent from said package and replacing it with a second agent where said second agent is adapted to inhibit microbial activity on the surface of said product; and
replacing said second agent with a third agent, where said third agent includes a high $O_2$ content.

12. The method of claim 11 where said first agent is drawn from the group consisting of $O_3$, $F_2$, $H_2O_2$, $KMnO_4$, $HClO$, $Cl_2$, $ClO_2$, $O_2$, $Br_2$ and $I_2$.

13. The method of claim 11 where said first agent is an oxidizing gas.

14. A method for processing a perishable product comprising the steps of:
sealing the product in a consumer-ready package;
introducing a first agent into said package where said agent is selected to reduce the microbial activity present on the surface of said product, where further said agent is introduced at a selected concentration as determined by the moisture of fat content of said product;
maintaining said first agent in said package for a residence time determined on the basis of the type and concentration of the agent;
extracting said first agent from said package and replacing it with a second agent where said second agent is adapted to inhibit microbial activity on the surface of said product; and
replacing said second agent with a third agent, where said third agent includes a high $O_2$ content.

15. The method of claim 14 further including the step of introducing yet a fourth agent into said package to enhance the aesthetic characteristics of said product, where said product is drawn from the group consisting of ascorbic acid, isoascorbic acid, erythorbic acid, lactic acid, citric acid, succinic acid and mixtures of salts thereof.

16. The method of claim 11 where said package is provided with a resealable valve through which said agents are introduced or extracted.

17. The method of claim 14 where said package is provided with a resealable valve through which said agents are introduced or extracted.

18. The method of claim 5 where the concentration of said agent is determined by the moisture of fat content of a meat product.

19. A method of processing a meat product comprising the steps of:
positioning a meat product in a package in gas communication with a selected first agent and thereafter sealing said package while gas communication is maintained between said product and said agent, where the concentration of said agent is determined by the moisture or fat content of the meat product.

* * * * *